(12) United States Patent
Poncon et al.

(10) Patent No.: US 8,047,482 B2
(45) Date of Patent: Nov. 1, 2011

(54) LOCK FOR FIXATION DEVICE

(75) Inventors: Gilbert Poncon, Pommiers la Placette (FR); Philippe Traversaz, Saint-Blaise du Buis (FR)

(73) Assignee: Fresenius Vial SAS, Brezins (FR)

( * ) Notice: Subject to any disclaimer, the term of this patent is extended or adjusted under 35 U.S.C. 154(b) by 89 days.

(21) Appl. No.: 12/523,415

(22) PCT Filed: Jan. 16, 2009

(86) PCT No.: PCT/EP2008/050454
§ 371 (c)(1),
(2), (4) Date: Aug. 18, 2009

(87) PCT Pub. No.: WO2008/090068
PCT Pub. Date: Jul. 31, 2008

(65) Prior Publication Data
US 2010/0065700 A1    Mar. 18, 2010

(30) Foreign Application Priority Data
Jan. 20, 2007   (FR) ...................................... 07 00393

(51) Int. Cl.
*A47B 96/06* (2006.01)
(52) U.S. Cl. .................... 248/205.1; 248/316.1; 604/250
(58) Field of Classification Search ............... 248/206.5, 248/309.1; 604/250
See application file for complete search history.

(56) References Cited

U.S. PATENT DOCUMENTS

| | | | |
|---|---|---|---|
| 2,692,153 A | 10/1954 | Schlueter | |
| 4,547,092 A * | 10/1985 | Vetter et al. | 403/59 |
| 4,832,299 A * | 5/1989 | Gorton et al. | 248/231.71 |
| 5,014,956 A | 5/1991 | Kayali | |
| 5,108,213 A * | 4/1992 | Shields | 403/18 |
| 5,174,533 A * | 12/1992 | Pryor et al. | 248/288.51 |
| 5,322,253 A * | 6/1994 | Stevens | 248/229.15 |
| 5,829,723 A | 11/1998 | Brunner et al. | |
| 6,315,260 B1 * | 11/2001 | Lees | 248/286.1 |

(Continued)

FOREIGN PATENT DOCUMENTS

FR    2881507 A1 *   4/2006

(Continued)

OTHER PUBLICATIONS

International Search Report of PCT/EP2008/050454, Mailing Date of Apr. 4, 2008.

*Primary Examiner* — Terrell McKinnon
*Assistant Examiner* — Daniel J Breslin
(74) *Attorney, Agent, or Firm* — Westerman, Hattori, Daniels & Adrian, LLP (57) ABSTRACT

A device for securing an object on a holder includes a platen attached to the object, a tightening element that pivots relative to the platen so that it can be folded back against the platen or raised perpendicularly to the platen. A lock is provided for locking the tightening element in the position perpendicular to the platen. The lock includes a tab that moves between a stowed position in which, when the tightening element is in the raised position, the tab bears against the tightening element and blocks it in this position, and a drawn out position in which the tab allows the tightening element to pivot towards the platen so that, in the folded position of the tightening element, the tab bears against a face of the tightening means different from the inner face.

27 Claims, 5 Drawing Sheets

U.S. PATENT DOCUMENTS

| | | | |
|---|---|---|---|
| 6,459,887 B2 * | 10/2002 | Okuda | 455/90.1 |
| 6,729,299 B2 * | 5/2004 | Anschicks et al. | 123/399 |
| 7,178,777 B1 * | 2/2007 | Banker | 248/316.7 |
| 2006/0079849 A1 * | 4/2006 | Zoltan et al. | 604/250 |

FOREIGN PATENT DOCUMENTS

| | | |
|---|---|---|
| FR | 2881507 A1 | 8/2006 |
| WO | 01-36027 A1 | 5/2001 |
| WO | 2006-082171 A1 | 8/2006 |

* cited by examiner

LOCK FOR FIXATION DEVICE

The invention concerns a device for securing of an object on a holder, which device is equipped with fixation means comprising a platen fixed to one of the walls of the object to be secured, preferably the rear wall, and tightening means for tightening the fixation means to the holder, the tightening means being capable of pivoting relative to the platen about an axis (N) so that they can be folded back against the platen or raised perpendicularly to said platen, locking means being provided to lock the tightening means in the operative position raised perpendicularly to the platen.

The fixation device of the invention is designed in particular for an object that must be secured in a preferred spatial position irrespective of the orientation of the holder. This is the case, for example, with a medical module such as a syringe pusher that can be secured to a vertical pole, to a horizontal rail, or in a rack. Irrespective of the holder to which is must be fixed, its spatial orientation must remain the same, i.e., the top of the syringe pusher must be at the top and the bottom at the bottom. In general, it is not possible to use these pumps in a "flat" position, i.e., pivoted by 90° relative to a horizontal axis.

A device conform from the preamble is known from FR 2 881 507 A1. The medical module is equipped, on its rear face, with fixation means that can pivot between two preferred positions to make it possible to secure it to a horizontal holder as well as to a vertical holder. These fixation means are constituted, firstly, by a platen fixed to the rear wall of the module so as to be able to pivot between two perpendicular positions, and secondly, by tightening means, in this case a tightening yoke equipped with a jaw and a tightening screw, which can pivot so that it can be, according to one's wishes, folded back against the platen, in particular for storage, or, on the contrary, raised to a position perpendicular to said platen, to make it possible to secure the module to the selected holder. Locking means are provided to prevent the tightening means from folding back by themselves when they are in the raised position. These locking means comprise a lock that pivots about a pivoting axis which coincides with the pivoting axis of the platen and which has an eccentric portion with a flat edge, which, when the lock is actuated, comes to bear against the inner face of the tightening means and prevents them from pivoting. When the lock is unlocked, the tightening means can be folded back thereon. In addition, to prevent the tightening means from being raised unexpectedly, retaining means are provided on the tightening means and/or on the platen in order to retain the tightening means against the platen, without blocking it, however, when the tightening means are in the position folded back against said platen. These retaining means are preferably constituted by magnets.

This device provides a high versatility of use because it can be secured to a horizontal support or to a vertical support, while permitting the fixation yoke to be folded back against the module during storage. The magnets prevent the yoke from rising during its storage, while the locking means prevent the yoke from folding back when the module is secured to its holder.

However, the locking operation is not always easy. That is, it is necessary, firstly, to maintain the yoke in its position raised perpendicularly to the platen, and secondly, to pivot the lock by a quarter-turn to block the yoke in this raised position. Either the lock will pivot easily, in which case the yoke is not securely blocked in raised position, which leaves some play when the module is fixed to its holder, or, on the contrary, the lock pivots only with difficulty, which ensures that the yoke is securely locked in raised position, but it requires a certain force to ensure that the yoke is securely locked. In this case, it is not rare that the personnel will give up locking the yoke correctly in its raised position. However, if the lock is not entirely rotated, the yoke is not correctly blocked and it is at risk of folding back during use, taking the module with it. In addition, the lock is located in the angle formed by the platen and the yoke, i.e., in a location that is not easily accessed.

The objective of the invention is to propose a fixation device according to the preamble, which makes it possible to lock the tightening means easily in their raised position. Another objective of the invention is to design the fixation device so that it is possible to avoid distinct retaining means, in particular, in the form of magnets.

The main objective is reached in accordance with the invention by the fact that the fixation means are constituted by a tab capable of displacement between a first, stowed position in which, when the tightening means are in the raised position, it is placed by a bearing surface against the inner face of said tightening means and blocks them in this position, and a second, drawn out position in which it allows the tightening means to pivot freely towards the folded position or the raised position while passing in front of the drawn out tab so that, in the folded position of the tightening means, the tab faces or bears against one of the faces of the tightening means different from the inner face. Thus, it is sufficient to move the tab away to allow the tightening means to pivot in one direction or the other, whereas, in the stowed position, it blocks these tightening means if they are in raised position. It is no longer necessary to pivot a lock placed in the angle formed by the tightening means and the platen.

In a particular embodiment of the invention, a spring is provided which tends to maintain the tab in the stowed position. In other words, as soon as the tightening means are raised, the tab assumes its blocking position automatically. In addition, even if the module or its holder are subjected to jolts, the tab remains in the stowed position and the module is not at risk of folding back at an untimely moment.

To make it possible to guide the tab automatically when the tightening means is raised without having to move it away manually, it is preferable to equip the outer edge of the tightening means with an inclined surface against which the tab can slide during pivoting of the tightening means between their folded position and their raised position. The tab, during this pivoting movement, passes around the outer edge of the tightening means against the force of the spring until it reaches beyond the outer edge and goes on to block the tightening means in their raised position.

This inclined surface serves as a cam for the tab. The latter is subjected to the force of the spring, which, irrespective of its position, tends to bring it back to its stowed position. When the tightening means are folded, the tab, under the action of the spring, bears on the inclined surface. The farther away the tightening means are moved from the folded position toward the raised position, the more the inclined surface forces the tab to move away from its stowed position until it has been sufficiently moved away to let the outer edge of the tightening means pass. As soon as this outer edge has passed the tab, the latter leaves the inclined surface and returns automatically to its stowed position under the action of the spring.

A second advantage of this solution is that it functions as retaining means. That is, the tab, by bearing on the inclined surface, tends to push the tightening means into their folded position. The tightening means can be raised only if the return force of the spring is overcome. The latter is dimensioned so that it is sufficiently strong to retain the tightening means in folded position even against the effect of gravity, but not too much so that the user can raise the tightening means without too much effort.

To unlock the tab when it is in its position locking the tightening means, it is preferable to equip it with an unlock button which can be pushed or pulled to move the tab into its drawn out position, possibly against the force of the spring.

The simplest way is to place the tab on the rotation axis of the tightening means. For example, the tab can be placed at the extremity of a rod that serves as the axle for the rotation of the tightening means. Similarly, the spring is preferably a compression spring, preferably placed inside the rotation axle of the tightening means. It is preferable to design the tab so that it can be moved between its two extreme positions by a translation movement.

According to the invention, the tightening means are equipped with actuating means disposed on said tightening means so that they can be manipulated from the lateral side of the fixation means. Thus, the operator can have access to the actuating means from the lateral side of the fixation means, and thus of the module, which is much more convenient than having to access them from the rear, as is often the case in the state of the art.

Preferably, to allow securing the module horizontally as well as vertically, the platen can pivot by 90° about an axis (P).

Preferably, the tightening means comprise a yoke equipped with a jaw and a tightening screw, both of which can pivot about the axis (N). This embodiment is particularly simple and convenient, easy to implement industrially.

Preferably, to facilitate the use of fixation means according to the invention, stop means are provided to limit the pivoting movement of the pivotable fixation means, preferably, between two extreme positions located at 90° from each other. Thus, the fixation means can take only two positions perpendicular to each other. However, it would also be possible to allow the pivotable fixation means to take four distinct positions shifted by 90° relative to each other, so as to provide two possible positions for each type of horizontal or vertical holder. For example, the stop means can consist of a guiding and stop spike integral with the platen and which cooperates with a guiding groove provided in the wall of the object to be secured, or vice versa.

It may be preferable to allow the tightening means to be raised only when the platen is in its use position, i.e., to prevent the tightening means from being raised in an intermediary position between two use positions. To this aim, it is possible to provide guiding means for guiding the pivoting movement of the tightening means into one or the other of the use positions. This can be performed, for example, by designing these guiding means in the form of a guiding rib provided on the tightening means and of at least one guiding groove provided in the wall of the object to be secured facing at least one of the use positions, and in which the guiding rib can be inserted when the tightening means pivot about axis (N) toward the use position. If the platen is not in one of the use positions, the rib will not be able to be enter into any of the guiding grooves. It will then block the pivoting movement of the tightening means toward the raised position. Thus, in order to raise the tightening means to the use position, the platen must be correctly positioned.

In order for the fixation device to be as stable as possible in open position, and for the object to be secured to be prevented from pivoting toward the side, it is preferable to provide an angular indexing at the end of the raising movement of the tightening means. To this effect, blocking means are provided to block the platen in at least one of its use positions, these blocking means comprising preferably an index placed on the tightening means, which is inserted into an indexing groove provided in the wall of the object to be secured when the tightening means are raised in use position. Whereas, in principle, the guiding means did not have to enable a movement without play, it is preferable for this angular indexing to be as precise as possible and without play.

Preferably, the fixation means comprise a groove whose dimensions correspond to the usual dimensions of the horizontal holders, said groove being preferably provided in the jaw of the tightening means. Thus, it is possible to place the module on a horizontal rail having a rectangular cross-section while preventing it from pivoting under the effect of its own weight before the tightening means are put in place. It is possible to provide for rails of various dimensions by imbricating several grooves in each other, from the largest to the narrowest.

In a variant embodiment of the invention, the fixation means are equipped with means for inserting the object to be secured into a location, for example, in a rack, said introduction means comprising preferably a spike parallel to the rear wall of the object and capable of performing a circular movement relative to the rear wall of the object to be secured, said spike being capable of being inserted into a guiding groove provided in one of the lateral walls of the location of the rack, so that the movement of the spike in the guiding groove causes the object to be secured to enter the location. By pivoting the platen about its axis (P), the spike penetrates into the guiding groove. The deeper it penetrates into this groove, the more it is constrained by the groove to advance toward the bottom of the location, while taking the module with it. Thus, it is not necessary to push the module to make it penetrate into the location, at the risk of toppling the whole rack.

It can be advantageous to provide a sensor to detect a good positioning of the object to be secured in the location, the sensor being preferably a Hall effect sensor cooperating with a magnet placed in the pivotable fixation means, preferably in the vicinity of the spike. For example, the sensor can be positioned close to the guiding groove, preferably in the vicinity of the terminal portion of said groove.

The invention also concerns locking means for a fixation device according to the invention, the locking means being characterized by a tab equipped with a bearing surface dimensioned so as be capable of cooperating with the inner surface of the tightening means, and also, as appropriate, by a rod that can serve as rotation axis (N) for the tightening means and/or by an unlock button that can be secured in particular to the other extremity of the rod and/or by a spring.

An exemplary embodiment of the invention is presented below in comparison with a device according to the state of the art. The Figures show.

Figure 1:
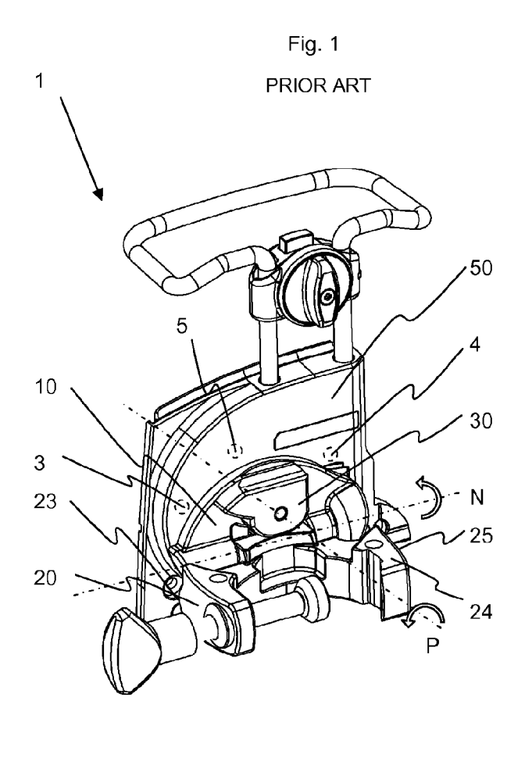
FIG. 1: a fixation device of the prior art in a position making it possible to secure it to a vertical holder.
Figure 2:
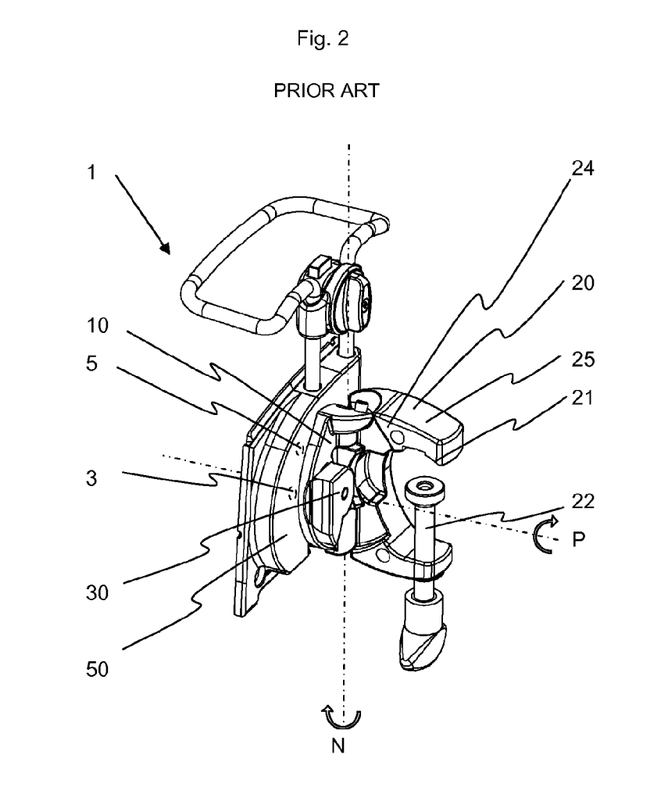
FIG. 2: the device of FIG. 1 in a position making it possible to secure it to a horizontal holder.

For improved clarity, FIGS. 1 and 2 show a fixation device (1) of the prior art, as it is known from document FR 2 881 507 A1. The fixation device of the invention (100) is an improvement of this known device (1). These two devices (1, 100) are composed essentially of three parts: a pivotable platen (10, 110), a pivotable yoke (20, 120) and a bolt (30, 130). The pivotable platen (10, 110) and the pivotable yoke (20, 120) constitute the fixation means, the pivotable yoke (20, 120) constituting the tightening means and the bolt (30, 130) the locking means.

The pivotable platen (10, 110) is fixed to the rear wall (50, 150) of the object to be secured. It can pivot by 90° about its axis (P).

Figure 7A:
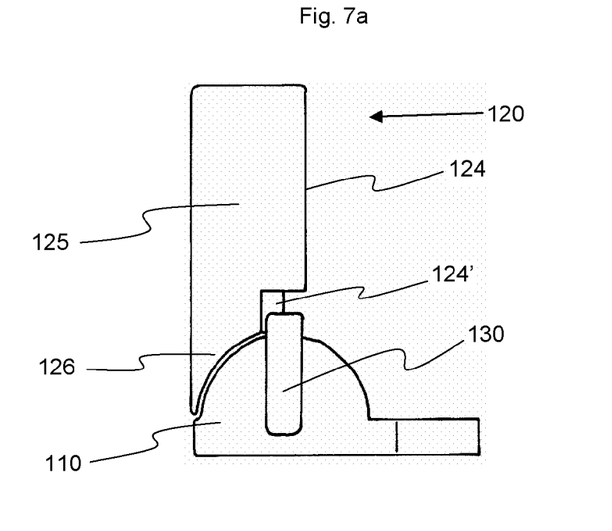
FIG. 7*a*-7*c*: schematic lateral views of the device of FIG. 3 with the tightening means (a) in raised position, (b) in intermediary position, and (c) in folded position.
Figure 7B:
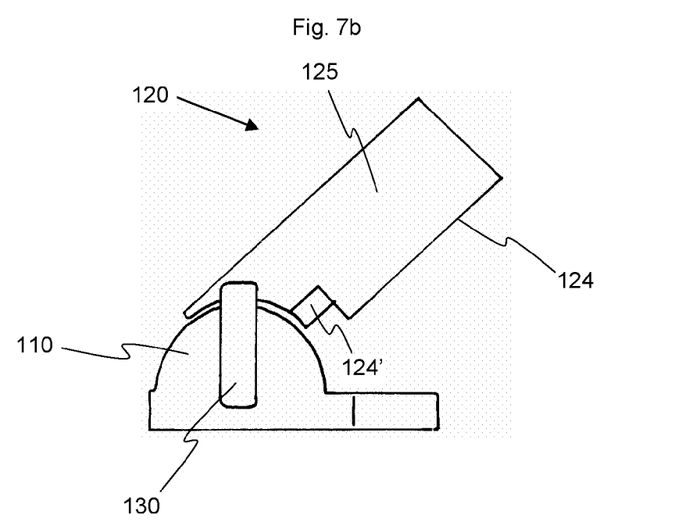
Figure 7C:
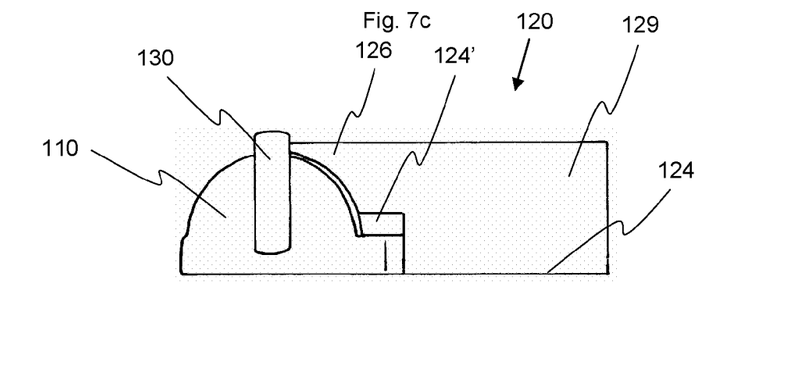

The pivotable yoke (20, 120) is constituted essentially by a jaw (21, 121) and a tightening screw (22, 122). It can be fixed to the platen (10, 110) so as to pivot about its axis (N) between a folded position and a raised position after having performed a quarter-turn about the axis (N). FIGS. 1 to 3 and 7a show the tightening means (20, 120) in the raised position, FIGS. 4 and 7b in an intermediary position, and FIGS. 5 and 7c in folded position.

The tightening means (20, 120) have an internal lateral face (24, 124) which, when it is folded, faces the platen (10, 110), an external lateral face opposed to the internal lateral face, two external edges (25, 125) and a rear face (23, 123), face that faces the platen when the tightening means (20, 120) are in raised position. This rear face (23, 123) can serve as a stop to prevent the tightening means from going beyond an angle of 90° when they come to bear on the rear wall (50, 150) of the object to be secured. Of course, other types of stops can be envisioned.

The tightening screw (22, 122) serves as actuating means for the tightening means. As shown in the Figures, it is always accessible from the lateral side of the fixation means, i.e., the lateral side of the module on which they are fixed, and this, whether the fixation means are raised or folded and whether they are in horizontal position or vertical position. The hand of the user does not need to search behind the module for a tightening screw that is raised perpendicularly to the rear face of this module.

For security reasons, the tightening means (20, 120) must be locked in their open position with the help of locking means. According to the invention, these locking means are constituted by a tab (130) that can be moved between a first stowed position (FIGS. 3 and 5) and a second drawn out position (FIG. 4).

Figure 3:
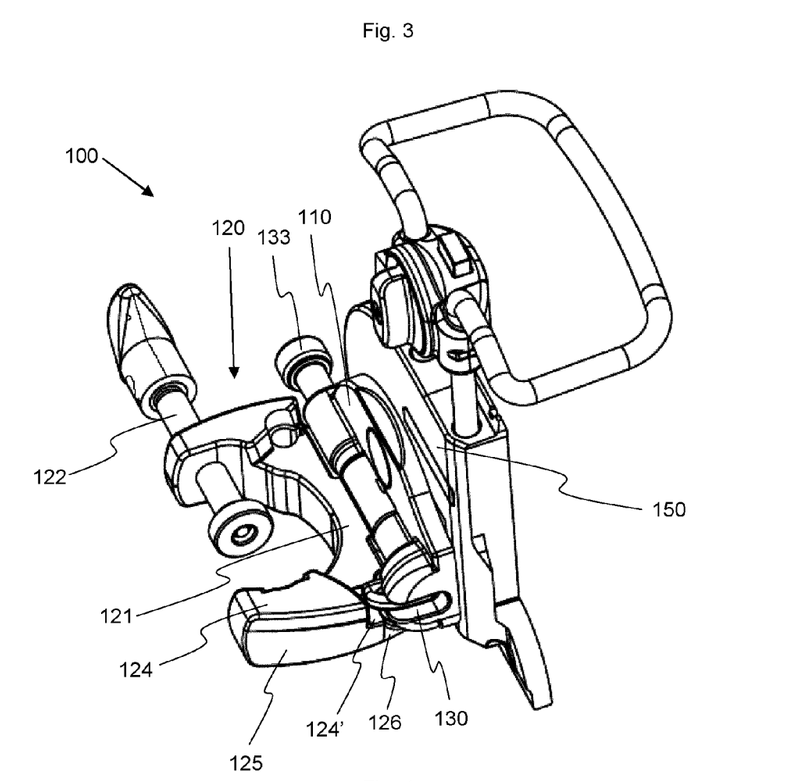
FIG. 3: the improved device according to the invention in raised position making it possible to secure it to a vertical holder, the locking means being in stowed position.

In the folded position of FIG. 3, if the tightening means are in raised position, the tab bears against the internal face (124) of the tightening means (120) and blocks them in this position. The tightening means (120) are thus blocked against any pivoting movement, firstly, by the tab (130) which prevents them from returning to the folded position, and secondly, by their rear faces (123) which serve a stops, preventing them from going beyond this position raised at 90°.

Figure 4:
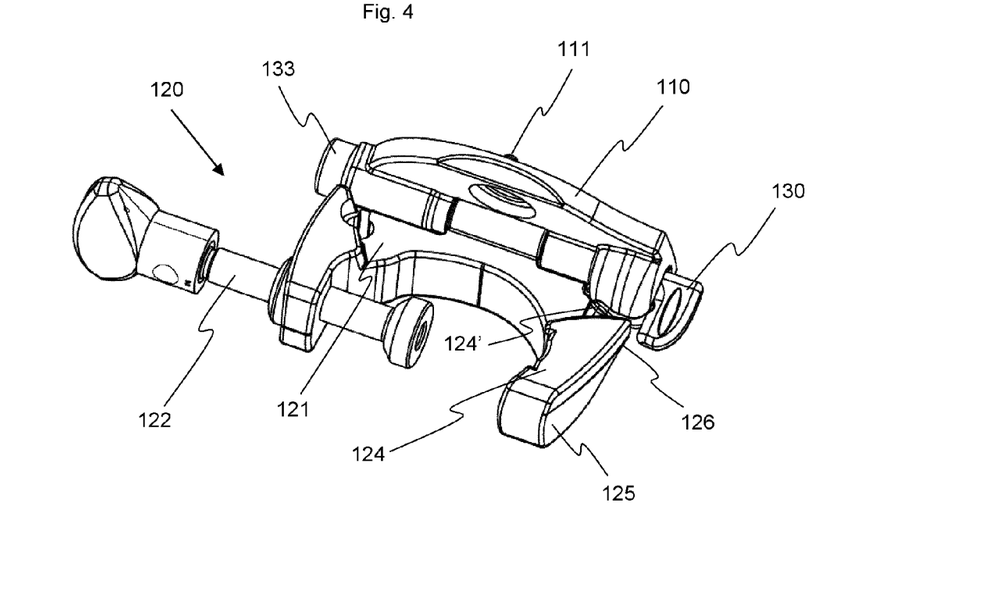
FIG. 4: the platen and the tightening means of the device of FIG. 3 with the tightening means in intermediary position and the locking means in drawn out position.

In the spread position of FIG. 4, the tab allows the tightening means (12) to pivot freely in direction of the platen (120) by passing in front of the drawn out tab (130). In folded position of the tightening means (120), the tab no longer faces the internal face (124), but it faces the external edge (125) as shown on FIGS. 5 and 7c. It would also be possible to have the tab bear against the lateral external face of the yoke after having passed beyond the external edge (125).

To simplify, the tab (130) is placed at the extremity of a rod (131) which also serves as the axis (N) for the pivot of the tightening means (120). Consequently, the platen (110) and the tightening means (120) are articulated with each other by this rod (131).

To ensure that the tab (130) is maintained in its stowed position when the tightening means (120) are raised, a spring (132) is provided, which tends to return the tab (13) into this security position. Consequently, to fold the tightening means (120) when they are locked in raised position, an unlock button (133) located on the rod (131) opposite the tab (130) must be pushed.

To control movement of the tab (130) automatically, the tightening means (120) are equipped with an inclined surface (126) located on their external edge (125). This inclined surface (126) extends from the external lateral face toward the internal lateral face (124) of the tightening means, while forming substantially an arc of a circle. The slope of this inclined surface (126) is such that its lower extremity located on the side of the external face is closer to the median plane of the tightening means (120), a plane perpendicular to the pivoting axis (N) of these tightening means, than its upper extremity located on the side of its internal face (124).

To lock the tightening means (120) in raised position efficiently and without play, the internal face (124) is also equipped with an inclined surface (124') against which the tab (13) slides as soon as it has left the upper extremity of the first inclined surface (126). This second inclined surface (124') diverges angularly only slightly from the axis (N) so that it is not possible to move the tab (130) away by attempting to fold the tightening means (120) toward the platen (110). This second inclined surface ensures that the tab (130) bears effectively, i.e., without play, against the internal face (124) of the tightening means (120). The tab, under the force of the spring (132), slides on this second inclined surface (124') and forces the tightening means to end their rising movement until they are substantially perpendicular to the platen (110). These two inclined surfaces (124', 126) are clearly visible on FIGS. 7a to 7c.

Thus, it is observed that when the tightening means (120) are folded against the platen (110), the tab (130) bears against the lower extremity of the inclined surface (126), in the vicinity of the external lateral face of the yoke (120). By raising the tightening means (120), the tab (130) is caused to slide on the inclined surface (126) and is moved away from its stowed position against the return force of the spring (132). This return effect of the spring (132) is sufficient, in the absence of sufficient solicitations, to maintain the tightening means (120) in folded position irrespective of their position. As a result, it is no longer necessary to use magnets as in the device of the state of the art.

By contrast, if the user overcomes the return force of the spring (132), he can raise the tightening means (120) until they reach the raised position perpendicular to the platen (110). During all of this movement, the tab (130) slides on the inclined surface (126) while moving more and more away from its stowed position (see FIGS. 7a to 7c). As soon as the raised position is reached, the tab (130) passes beyond the upper extremity of the inclined surface (126). Having lost its support, it falls back under the return force of the spring (132) into its rest position, the stowed position, by sliding against the second inclined surface (124') which is much more slanted than the first. The tightening means (120) are thus locked in their working position.

To fold the tightening means (120), the user only needs to push on the unlock button (133). The tab (130) is then moved away from its rest position to an extent sufficient to let the tightening means (120) pivot freely about the axis (N) while passing in front of this tab (130) which has been moved away.

As in the prior art, in the open position, the tightening means (120) can take two distinct positions shifted by 90° relative to each other. The object to be secured can thus be secured to a vertical pole when the tightening means (120) are raised in horizontal position (FIG. 1) or to a horizontal rail when they are raised in vertical position (FIG. 2). Thus, the same fixation means make it possible to secure the object in a preferred spatial position.

Figure 5:
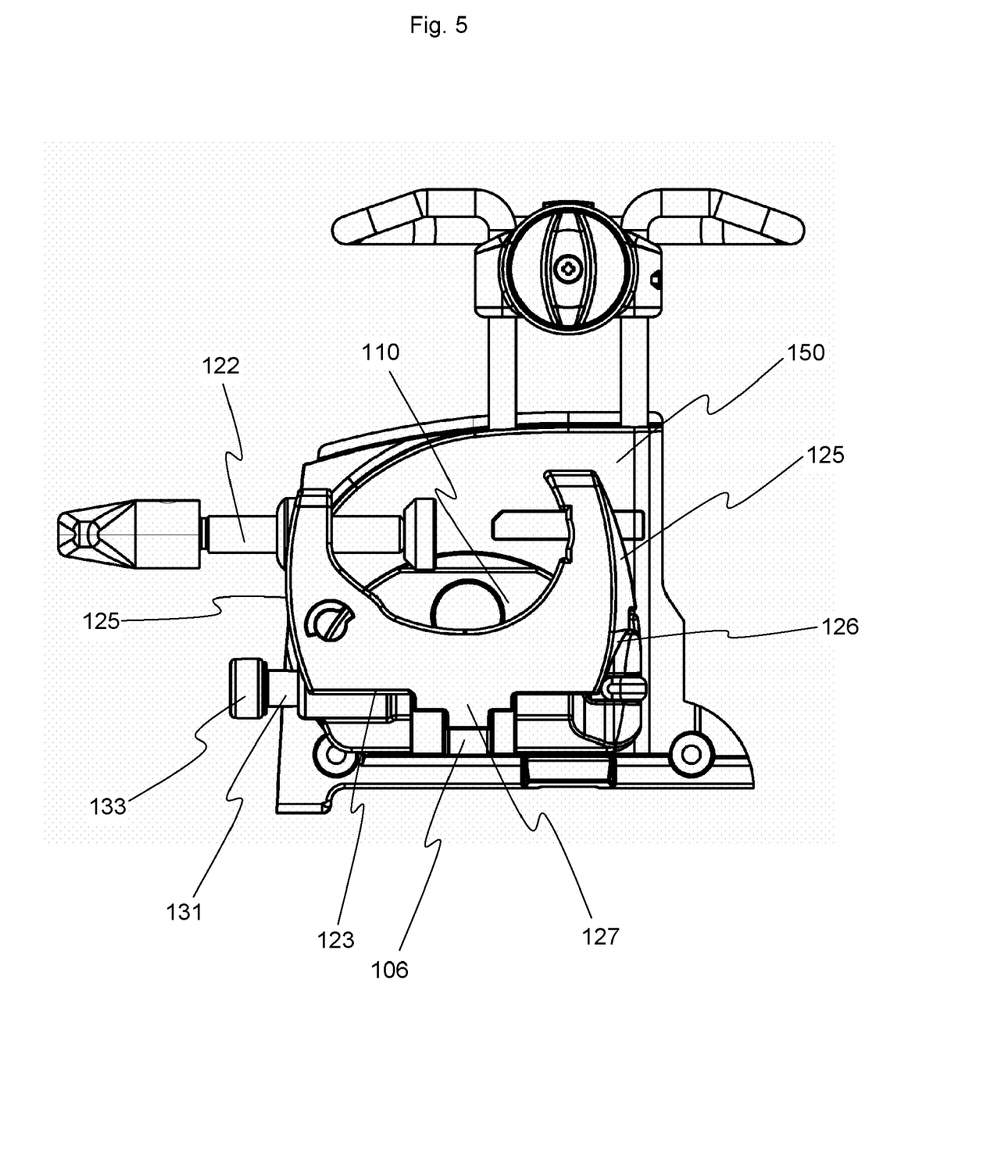
FIG. 5: the device of FIG. 3 with the tightening means in folded position and the locking means in stowed position.
Figure 6:
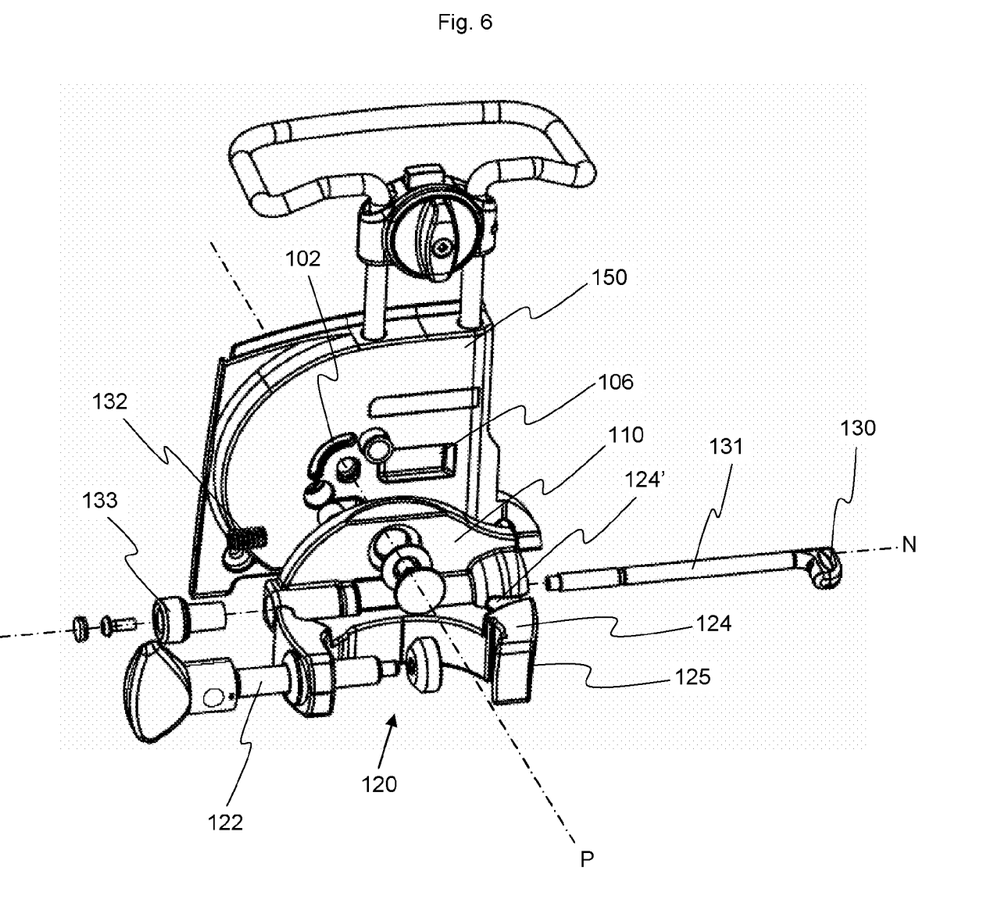
FIG. 6: an exploded view of the device of FIG. 3.

FIG. 5 shows a guiding rib (127) provided on the tightening means and intended for cooperating with at least one guiding groove provided in the wall of the object to be secured facing at least one of the use positions of the platen, and in which the guiding rib can be inserted when the tightening means pivot about axis (N) toward the use position.

LIST OF REFERENCES

| Prior art (FIGS. 1 and 2) | Invention (FIGS. 3 to 7) | |
|---|---|---|
| 1 | 100 | Fixation device |
| | 102 | Pivot groove for the platen |
| | 106 | Guiding groove |
| 10 | 110 | Pivoting platen |
| | 111 | Guiding and stop spike |
| 20 | 120 | Pivoting yoke |
| 21 | 121 | Jaw |
| 22 | 122 | Tightening screw |
| 23 | 123 | Rear face of the yoke |
| 24 | 124 | Inner lateral face of the yoke |
| 25 | 125 | Outside edge |
| | 126 | Inclined surface |
| | 127 | Guiding groove |
| 30 | 130 | Lock/tab |
| | 131 | Rod |
| | 132 | Spring |
| | 133 | Unlock button |
| 50 | 150 | Rear face of the object to be secured |

The invention claimed is:

1. Device for securing an object on a holder, which device comprises:

(i) fixation means comprising:

a platen to be fixed to one of the walls of the object to be secured, and tightening means for tightening the fixation means to the holder, the tightening means being pivotable relative to the platen about an axis (N) so that they can be folded back against the platen in a folded position and raised perpendicularly to said platen in a raised position, said tightening means having a lateral exterior face which faces the platen in the folded position of the tightening means, and (ii) locking means provided to lock the tightening means in the use position perpendicular to the platen, wherein the locking means comprise a tab mobile between a first, stowed position in which, when the tightening means are in the raised position, a bearing surface of said tab is placed against the lateral exterior face of said tightening means and blocks said tightening means in the raised position, and a second, drawn out position in which said tab allows the tightening means to pivot freely towards the platen while passing in front of the drawn out tab so that, in the folded position of the tightening means, the tab faces or bears against a face of the tightening means different from the lateral exterior face.

2. Device according to claim 1, wherein a spring is provided which tends to maintain the tab in the stowed position.

3. Device according to claim 2, wherein an outer edge of the tightening means is equipped with an inclined surface against which the tab can slide when the tightening means pivot between their folded position and their raised position, wherein the tab, during this pivoting movement, passes around the outer edge of the tightening means against the force of the spring until it reaches beyond the outer edge and goes on to block the tightening means in their raised position.

4. Device according to claim 1, wherein the tab is equipped with an unlock button which can be pushed or pulled to move the tab in its drawn out position.

5. Device according to claim 1, wherein the tab is placed on a rotation axis of the tightening means relative to the platen.

6. Device according to claim 2, wherein the spring is a compression spring.

7. Device according to claim 1, wherein the tightening means are equipped with actuating means disposed on the tightening means so that the actuating means is configured to be manipulated from a lateral side of the fixation means.

8. Device according to claim 1, wherein the tightening means comprise a yoke equipped with a jaw and a tightening screw, both of which pivot about the axis (N).

9. Device according to claim 1, wherein the platen is fixed to an object and configured to pivot by 90 degrees about an axis (P) relative to the object, so as to secure the object indifferently to a vertical holder or to a horizontal holder.

10. Device according to claim 9, wherein stop means are provided to limit the pivoting movement of the pivotable platen between two extreme positions.

11. Device according to claim 9, wherein guiding means are provided for guiding the pivoting movement of the tightening means into one or the other of the use positions.

12. Device according to claim 1, wherein the pivotable fixation means comprise a positioning groove on the tightening means for fitting the tightening means on a horizontal holder.

13. Device according to claim 1, wherein the tab is secured to a rod that serves as the rotation axis (N) for the tightening means.

14. Device according to claim 4, wherein the unlock button is pushed or pulled to move the tab in its drawn out position against the force of a spring.

15. Device according to claim 6, wherein the compression spring is placed inside the rotation axis (N) of the tightening means.

16. Device according to claim 10, wherein the stop means comprise a guiding and stop spike integral with the platen and which cooperates with a guiding groove provided in the wall of the object to be secured, or vice versa.

17. Device according to claim 10, wherein the two extreme positions are located at 90° from each other.

18. Device according to claim 11, wherein the guiding means comprise a guiding rib provided on the tightening means and at least one guiding groove provided in the wall of the object to be secured facing at least one of the use positions, wherein the guiding rib is inserted when the tightening means pivot about axis (N) toward the use position.

19. Device according to claim 12, wherein the positioning groove is provided in the jaw of the tightening means.

20. Device according to claim 1, wherein the face of the tightening means which the tab faces or against which the tab bears in the folded position of the tightening means is an exterior face of the tightening means.

21. Device according to claim 20, wherein the tab is received in a U-shaped slot of the platen.

22. Device according to claim 20, wherein the tab moves between the first, stowed position and the second, drawn out position by a translation along the direction of the axis (N) without rotation around the direction of axis (N).

23. Device according to claim 22, wherein the tab is received in a U-shaped slot of the platen.

24. Device according to claim 22, wherein the locking means comprise an unlock button secured to a first extremity of a rod, the tab being secured to a second extremity of the rod.

25. Device according to claim 1, wherein the tab moves between the first, stowed position and the second, drawn out position by a translation along the direction of the axis (N) without rotation around the direction of axis (N).

26. Device according to claim 25, wherein the tab is received in a U-shaped slot of the platen.

27. Device according to claim 25, wherein the locking means comprise an unlock button secured to a first extremity of a rod, the tab being secured to a second extremity of the rod.

* * * * *